US00PP13435P2

(12) United States Plant Patent
Moolenaar

(10) Patent No.: US PP13,435 P2
(45) Date of Patent: Dec. 31, 2002

(54) ALLAMANDA PLANT NAMED 'BCT9810ALL'

(75) Inventor: Alfred Nicol Moolenaar, Voorhout (NL)

(73) Assignee: BCT Bio Chemical Technologies AG, Zug (CH)

( * ) Notice: Subject to any disclaimer, the term of this patent is extended or adjusted under 35 U.S.C. 154(b) by 0 days.

(21) Appl. No.: 10/014,465

(22) Filed: Dec. 8, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Allamanda plant named 'BCT9810ALL', characterized by its upright, spreading and trailing growth habit; freely flowering habit; and double flowers that are yellow in color.

1 Drawing Sheet

BOTANICAL CLASSIFICATION/CULTIVAR DESIGNATION

*Allamanda hybrid* cultivar BCT9810ALL.

BACKGROUND OF THE INVENTION

The present Invention relates to a new and distinct cultivar of Allamanda plant, botanically known as *Allamanda hybrid,* and hereinafter referred to by the name 'BCT9810ALL'.

The new cultivar is a product of a planned breeding program conducted by the Inventor in Voorhout, The Netherlands. The objective of the breeding program was to develop new Allamanda cultivars with double flowers with attractive coloration.

The new cultivar originated from a cross-pollination of two unnamed selections of *Allamanda hybrid,* not patented, in Voorhout, The Netherlands. The new cultivar was discovered and selected by the Inventor as a flowering plant within the progeny from this cross-pollination in a controlled environment in Voorhout, The Netherlands, in 1998. The new cultivar was selected on the basis of its double yellow-colored flowers.

Asexual reproduction of the new cultivar by terminal cuttings taken in Voorhout, The Netherlands, since 1998, has shown that the unique features of this new Allamanda are stable and reproduced true to type in successive generations.

SUMMARY OF THE INVENTION

Plants of the cultivar BCT9810ALL have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'BCT9810ALL'. These characteristics in combination distinguish 'BCT9810ALL' as a new and distinct cultivar of Allamanda:

1. Upright, spreading and trailing growth habit.
2. Freely flowering habit.
3. Double flowers that are yellow in color.

Plants of the new Allamanda differ primarily from plants of the unnamed parent selections primarily in flower form as plants of the unnamed parent selections do not have single flowers.

Plants of the new Allamanda can be compared to plants of the cultivars Silver Dwarf and Hendersonii, not patented. In side-by-side comparisons conducted by the Inventor in Voorhout, The Netherlands, plants of the new Allamanda differed from of the cultivars Silver Dwarf and Hendersonii in the following characteristics:

1. Plants of the new Allamanda had darker green-colored, rounded and more pointed leaves than plants of the cultivars Silver Dwarf and Hendersonii.
2. Plants of the new Allamanda had larger flowers and were more freely flowering than plants of the cultivars Silver Dwarf and Hendersonii.
3. Plants of the new Allamanda had double flowers whereas plants of the cultivars Silver Dwarf and Hendersonii had single flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Allamanda.

The photograph at the top of the first sheet comprises a side perspective view of a typical flowering plant of 'BCT9810ALL'.

The photograph at the bottom of the sheet comprises a close-up view of typical flowers and leaves of 'BCT9810ALL'. Plants used in the photographs were about one year old.

DETAILED BOTANICAL DESCRIPTION

In the following description, color references are made to The Royal Horticultural Society Colour Chart, 2001 Edition, except where general terms of ordinary dictionary significance are used. Plants used for the following description were about 6 to 7 months old and grown in 17-cm containers in a glass-covered greenhouse in Voorhout, The Netherlands. Cuttings were harvested in February and the description was taken in early August. During the production of the plants, day temperatures were about 19° C. and night temperatures were about 17° C. The following measurements and values represent averages taken from a group of typical flowering plants.

Botanical classification: *Allamanda hybrid* cultivar BCT9810ALL.

Parentage:

*Female, or seed, parent.*—Unnamed selection of *Allamanda hybrid,* not patented.

*Male, or pollen, parent.*—Unnamed selection of *Allamanda hybrid,* not patented.

Propagation:

*Type cutting.*—Terminal cuttings.

*Time to initiate roots, summer.*—About 21 days at 23° C.

*Time to initiate roots, winter.*—About 25 days at 23° C.

*Time to produce a rooted cutting, summer and winter.*—About 28 to 35 days at 23° C.

*Root description.*—Numerous, thick and freely branching.

Plant description:

*Form.*—Flowering plant; initially upright, then spreading and trailing, typically requiring support to maintain upright habit. Plants are typically pinched after planting to enhance lateral branch development; about five lateral branches develop below the pinch.

*Plant height (length).*—About 1.8 meters.

*Plant diameter.*—About 1.2 meters.

*Growth rate.*—Plants grow more than 20 cm per month; vigorous.

*Lateral branches.*—Length: About 1.7 meters. Diameter: About 5 mm. Internode length: About 12 cm. Shape: Round in cross-section. Aspect: Initially upright, then spreading and trailing, requires support. Strength: Flexible, strong. Texture: Young stems, pubescent; mature stems, sparsely pubescent to glabrous. Color: Young stems: 143B to 143C. Mature stems: N199A.

*Foliage discription.*—Arrangement: In whorls of four; simple. Quantity per lateral branch: About 48. Length: About 11 cm. Width: About 3 cm. Shape: Oblanceolate. Apex: Apiculate. Base: Cuneate. Margin: Entire. Texture: Upper surface, glabrous; lower surface, pubescence along primary veins. Luster: Upper surface, shiny; lower surface, dull. Venation pattern: Pinnate. Petiole length: About 3 mm. Petiole diameter: About 2 mm. Color: Developing leaves, upper surface: 143A. Developing leaves, lower surface: 143B to 144A. Fully expanded leaves, upper surface: 143A. Fully expanded leaves, lower surface: 143C. Venation, upper surface: 143A. Venation, lower surface: 142D. Petiole: 143B to 143C.

Flower description:

*Flower type and habit.*—Double salverform flowers arranged in terminal cymes with about four flowers per cyme; about 20 flowers and flower buds per plant. Flowers face outward to slightly drooping. Flowers not persistent.

*Natural flowering season.*—Mid-summer in Voorhout, The Netherlands; flowering continuous during this period.

*Flower longevity on the plant.*—About one week.

*Fragrance.*—Sweet, pleasant.

*Inflorescence length.*—About 7 cm.

*Inflorescence diameter.*—About 14 cm.

*Flower buds.*—Length: About 4.5 mm. Diameter: About 1.2 cm. Shape: Oblong. Color: 150A to 150B.

*Flowers.*—Appearance: Flared trumpet, outer corolla fused, five-parted; stamens transformed into petaloids. Diamerter: About 5 cm. Depth (length): About 8 cm. Tube length: About 7 cm.

*Corolla.*—Arrangement/appearance: Single whorl of five petals, fused into flared trumpet; apices reflexed. Petal length: About 9 cm. Petal width: About 2.3 cm. Petal shape: Oblanceolate to roughly spatulate. Petal apex: Rounded to retuse. Petal margin: Entire. Petal texture: Smooth. Color: Petal, when opening, upper surface: 5A. Petal, when opening, lower surface: 5B. Petal, fully opened, upper surface: 5A. Petal, fully opened, lower surface: 5B to 6B.

*Petaloids.*—Arrangement: One or two whorls of ten petaloids. Length: About 3.5 cm. Width: About 2.3 cm. Shape: Irregularly oblanceolate to spatulate and flabellate. Apex: Rounded to retuse. Margin: Entire, undulate. Texture: Smooth. Color: When opening, upper and lower surfaces: 3A to 3B. Fully opened, upper and lower surfaces: 5A.

*Sepals.*—Arrangement/appearance: Five per flower; calyx cupped-shaped. Length: About 1.4 cm. Width: About 4 mm. Shape: Lanceolate to elliptic. Apex: Acute. Base: Cuneate. Margin: Entire. Texture: Smooth. Color: Developing sepals, upper surface: 143C to 144B. Developing sepals, lower surface: 144C. Fully expanded sepals, upper and lower surfaces: 144B to 144C.

*Peduncles.*—Length: About 2 cm. Diameter: About 2 mm. Angle: About 30 to 75° from vertical. Strength: Flexible, but strong. Color: 144B to 144C.

*Pedicels.*—Length: About 6 mm. Diameter: About 1.5 mm. Angle: Erect to about 20° from vertical. Strength: Flexible, but strong. Color: 144B to 144C.

*Reproductive organs.*—Stamens: All stamens are transformed into petaloids. Pistils: Quantity per flower: Two, rudimentary. Pistil length: About 4 mm. Stigma shape: Narrowly deltoid. Stigma color: Close to 202A. Style length: About 4 mm. Style color: 1C. Ovary color: 144B to 144C.

*Seed/fruit.*—Seed and/or fruit production has not been observed.

Disease/pest resistance: Plants of the new Allamanda have not been noted to be resistant to pathogens and pests common to Allamanda.

Weather tolerance: Plants of the new Allamanda have been observed to be tolerant to rain and wind and tolerant to temperatures from 1 to 35° C.

It is claimed:

1. A new and distinct cultivar of Allamanda plant named 'BCT9810ALL', as illustrated and described.

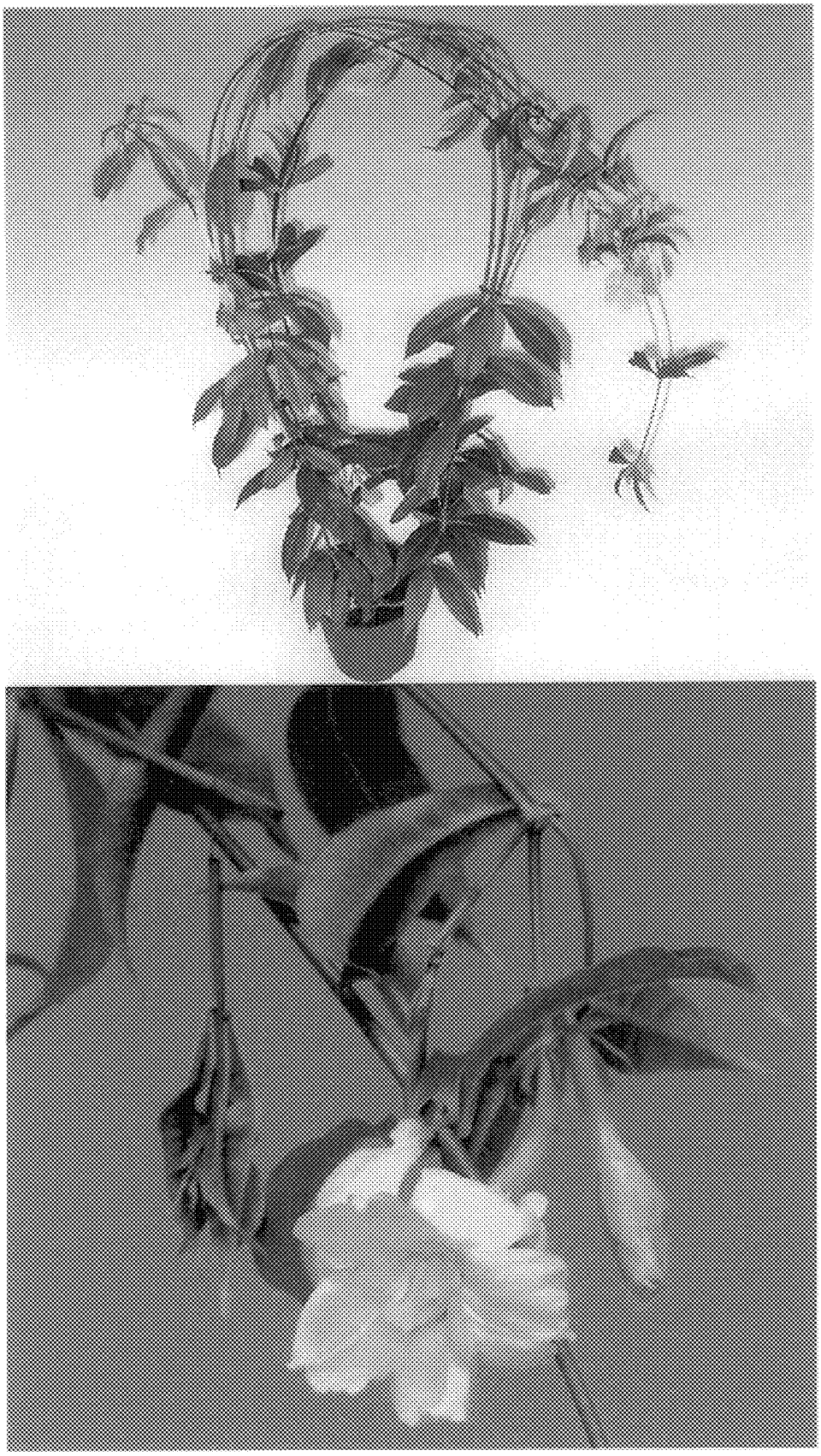

* * * * *